US010457888B2

(12) United States Patent
Stephens et al.

(10) Patent No.: US 10,457,888 B2
(45) Date of Patent: Oct. 29, 2019

(54) LUBRICATING MEMBERS FOR RAZOR CARTRIDGES

(71) Applicant: The Gillette Company, Boston, MA (US)

(72) Inventors: Alison Fiona Stephens, Maidenhead (GB); Poppy Clea Reese, Horsham (GB)

(73) Assignee: Braun GMBH, Kronberg (DE)

(*) Notice: Subject to any disclaimer, the term of this patent is extended or adjusted under 35 U.S.C. 154(b) by 0 days.

(21) Appl. No.: 15/193,177

(22) Filed: Jun. 27, 2016

(65) Prior Publication Data
US 2017/0002287 A1 Jan. 5, 2017

(30) Foreign Application Priority Data

Jun. 30, 2015 (EP) .................................... 15174439

(51) Int. Cl.
C10M 169/04 (2006.01)
A61K 8/31 (2006.01)
A61K 8/34 (2006.01)
A61Q 9/02 (2006.01)
A61K 8/894 (2006.01)
A61K 8/02 (2006.01)
B26B 21/44 (2006.01)
C10M 111/04 (2006.01)

(52) U.S. Cl.
CPC ......... C10M 169/04 (2013.01); A61K 8/0216 (2013.01); A61K 8/31 (2013.01); A61K 8/342 (2013.01); A61K 8/894 (2013.01); A61Q 9/02 (2013.01); B26B 21/443 (2013.01); C10M 111/04 (2013.01); A61K 2800/87 (2013.01); C10M 2203/10 (2013.01); C10M 2203/1006 (2013.01); C10M 2205/143 (2013.01); C10M 2207/021 (2013.01); C10M 2207/0215 (2013.01); C10M 2207/2815 (2013.01); C10M 2207/401 (2013.01); C10M 2227/045 (2013.01); C10M 2229/025 (2013.01); C10M 2229/0475 (2013.01); C10N 2220/021 (2013.01); C10N 2230/06 (2013.01); C10N 2230/08 (2013.01); C10N 2250/08 (2013.01)

(58) Field of Classification Search
CPC ...... C10M 2229/025; C10M 2203/102; C10N 2250/08; C10N 2270/00
USPC ............................................ 508/202; 44/250
See application file for complete search history.

(56) References Cited

U.S. PATENT DOCUMENTS

| | | |
|---|---|---|
| 4,170,821 A | 10/1979 | Booth |
| 5,134,775 A | 8/1992 | Althaus et al. |
| 5,711,076 A | 1/1998 | Yin et al. |
| 6,298,558 B1 | 10/2001 | Tseng et al. |
| 6,301,785 B1 | 10/2001 | Kwiecien et al. |
| 6,442,839 B1 | 9/2002 | Tseng et al. |
| 7,121,754 B2 | 10/2006 | Bressler et al. |
| 8,524,207 B2 | 9/2013 | Ellis et al. |
| 2006/0225285 A1 | 10/2006 | Slavtcheff et al. |
| 2007/0110703 A1 | 5/2007 | O'Grady et al. |
| 2008/0060201 A1 | 3/2008 | Kwiecien |
| 2008/0081055 A1* | 4/2008 | Cassin ................. A61K 8/0208 424/401 |
| 2009/0223057 A1 | 9/2009 | Coope-Epstein et al. |
| 2012/0272983 A1 | 11/2012 | Stephens et al. |
| 2013/0118014 A1* | 5/2013 | Stephens et al. ............. 508/202 |
| 2017/0000721 A1 | 1/2017 | Bradford et al. |

FOREIGN PATENT DOCUMENTS

| | | |
|---|---|---|
| GB | 1299089 | 12/1972 |
| GB | 2491406 | 12/2012 |

OTHER PUBLICATIONS

EPO Search Report with Written Opinion in corresponding EPO application 15174439.8 dated Jan. 18, 2016.
Momentive Performance Materials, "Silwet* Copolymers Chameleon Solutions," Created Nov. 17, 2011 (© 2011).

* cited by examiner

Primary Examiner — Vishal V Vasisth
(74) Attorney, Agent, or Firm — Ronald T. Sia; Kevin C. Johnson

(57) ABSTRACT

The invention relates to a lubricating member for a razor cartridge comprising a lipophilic structurant and a silicone polyether block copolymer and optionally a liquid phase, which can be manufactured in a simple one batch process without thermal degradation and exhibiting improved lubricating and skin care properties over a sustained period.

14 Claims, No Drawings

LUBRICATING MEMBERS FOR RAZOR CARTRIDGES

FIELD OF THE INVENTION

The invention relates to lubricating member for razor cartridges comprising a silicone polyether copolymer and a lipophilic structurant which exhibits improved lubricating properties.

BACKGROUND OF THE INVENTION

The use of shaving aids on razor blades to provide lubrication benefits during the shave is known. See e.g., U.S. Pat. Nos. 7,121,754; 6,298,558; 5,711,076; 5,134,775; 6,301,785, U.S. 2009/0223057 and US 2006/0225285. Such shaving aids typically comprise a water-insoluble matrix material to provide structural integrity and a water-soluble polymer, such as polyethylene oxide (polyox), in order to provide the lubrication during the shave once the water-soluble polymer forms a solution with the water present during shaving. Since the introduction of polyox as a shaving lubricant, little development has been made in the field, even though polyethylene oxide polymers are not without limitations. For example, the use of polyethylene oxide polymers having a low molecular weight only provides limited lubrication, and while improved lubrication may be seen when using polyethylene oxide polymer having higher molecular weights, this negatively impacts other aspects of the aqueous solution typically formed in-use. The resultant viscosity in aqueous solution may also increase, leading to negatively perceived attributes, for example concerning the feeling of the shave for the user, particularly in respect of the lubricant. The prior art does also describe the use of combinations of high and low molecular weight polyethylene oxide polymers in order to balance these performance attributes. Nevertheless, such combinations are also limited in their ability to improve performance and or suffer from other negative performance attributes.

The art further describes the incorporation of additional materials to further improve the lubrication performance. WO2007/031793 describes solid compositions for shaving apparatus comprising soap or surfactant and a skin enhancing additive. WO2012/148939 describes an erodible solid moisturizer comprising a modifying surfactant and a hydrophobic phase for hair removal devices. GB2491406 describes liquid replenishment of a shaving aid. GB1299089 describes liquid lubricating compositions comprising tri-functional polydimethylsiloxanepoly-oxyalkylene block copolymer, a lubricant and a propellant. U.S. Pat. No. 6,442,839 and US2007/0110703 describe the use of low levels of mineral and essential oils, butters, waxes and silicones. The use of mineral oil to enhance the glide performance is described in US2008/0060201. However the art also discloses that the presence of oils results in a reduction of the swelling and solubility of the water soluble shaving aid in the water insoluble polymer matrix. The ability of the shaving aid to swell in contact with water is however believed to be the key mechanism by which the lubrication benefit is delivered to the skin. Hence this is not desirable, as it will negatively impact the overall performance Thus oils are typically avoided in the matrix Another limitation of such shaving aids is related to the manufacturing process which typically involves an injection molding or extrusion process step. These processes require elevated temperatures in order to melt all the component materials and then subsequently mix them together and then injection mold or extrude. Consequently, the manufacture of such shaving aids is limited to low levels of additives and or materials which are not degraded by such process conditions. Nevertheless, the presence of even low levels of such additives in the manufacturing process can result in barrel slip and conveying inconsistencies which is also undesirable. Furthermore, the efficacy of desirable lubricants such as polyethylene oxide may also be negatively impacted by these manufacturing processes.

US2009/0223057 describes a razor shaving aid material that will last for an extended period of time and that can be manufactured at temperatures to avoid thermal degradation of ingredients, comprising a water soluble shaving aid, a water insoluble erodible medium that has a melting point above 45° C. and a molecular weight below 25000, wherein the water soluble shaving aid is soluble with the water insoluble erodible medium. The compatibility of the water soluble material and the water insoluble erodible material favorably influences the longevity of the shaving aid material. This manufacturing process is still complex however requiring multiple steps and component phase compatibility. Furthermore the improved longevity results in a shaving aid which is hard and brittle and which does not deposit sufficiently during use. Furthermore, the shaving aid is still also limited with regard to the addition of additives, which must also be compatible in the matrix.

Consequently there is still a need to provide a lubricating member for razor cartridges which can be manufactured in a simple one batch process exhibiting lubricating properties over a sustained period which can be readily manufactured without impacting performance due to thermal degradation of the ingredients such as polyethylene oxide and which can accommodate additional additives to provide desirable skin care benefits, especially in the liquid form such as oils.

SUMMARY OF THE INVENTION

One aspect of the invention relates to a lubricating member for use on a hair removal device, Comprising:
 a) from 10% to 80% by weight of a lipophilic structurant,
 b) from 0.1% to 60% by weight of a silicone polyether block copolymer, wherein said silicone polyether block copolymer comprises from 1% to 50%, by weight of polyethylene oxide, from 20% to 90% by weight of polypropylene oxide and from 1% to 20% by weight of silicone and
 c) optionally from 10% to 70% by weight of a liquid phase and
 d) optionally comprising less than 5% by weight of water insoluble polymeric structurant and less than 5% by weight of water soluble polymer.

Another aspect of the invention relates to the manufacture of a lubricating member comprising the steps of melting said lipophilic structurant at a temperature of about 85° C. and stirring, adding said silicone polyether block copolymer and stirring, cooling the resultant mixture to about 55° C., adding optional ingredients whilst stirring, and transferring the molten mixture into a mold or container.

DETAILED DESCRIPTION OF THE INVENTION

Lipophilic Structurant

According to the invention the lubricating member comprises from about 1%, preferably from about 10% to about 80%, more preferably about 20% to about 70%, even more preferably from about 25% to about 50% and even more preferably from about 25% to about 35% by weight of a lipophilic structurant.

The melting point of the lipophilic structurant is preferably from at least 45° C. to less than 90° C., more preferably from 45° C. to less than 60° C. and thus the lipophilic structurant is preferably a solid at 25° C. The melting point is determined according to ASTM D5440-93. If the lipophilic structurant comprises more than one material, the melting point is determined for the resultant mixture as described hereinafter. The lipophilic structurant is preferably water insoluble. The lipophilic structurant provides a chassis to contain the ingredient components which also deliver lubrication to the skin and other benefit agents during the shaving process.

Suitable lipophilic structurants for use herein include C14 or greater, preferably C14 to C20, more preferably C16 to C18 chain length fatty acyls such as fatty acids, fatty alcohols and esters, triglycerides, waxes and mixtures thereof. Particularly preferred are C14-C20 alcohols, in particular cetyl and stearyl alcohols and mixtures thereof.

Suitable lipophilic structurants include natural, synthetic and silicone waxes. As used herein, the term "wax" includes, but is not limited to, any material that is solid at 25° C.; very slightly soluble in water, preferably practically insoluble in water according to the United States' Pharmacopeia (USP) definition in 31/NF 26 Vol. 2 General Notices, Page Xvii. According to that definition, this means that 1000 to 10000 parts of water are needed to dissolve 1 part solute and that more than 10,000 parts of water are needed to dissolve 1 part solute respectively.

The wax may comprise natural wax, synthetic wax or mixtures thereof. Natural waxes may be plant, animal or mineral derived. Non-limiting examples of suitable natural waxes include Beeswax, *Copernicia Cerifera* (Carnauba) Wax, *Euphorbia Cerifera* (Candelilla) Wax, Jojoba Wax, *Oryza Sativa* (Rice) Bran Wax, Lemon peel wax, Soybean wax, Sunflower wax and mixtures thereof.

Non-limiting examples of suitable synthetic waxes include Hydrogenated Jojoba Wax, synthetic and siliconyl jojoba wax, Hydrogenated Microcrystalline Wax, Microcrystalline Wax, synthetic, siliconyl and Hydrogenated Rice Bran Wax, Ceresin, Ozokerite, Paraffin, benhenyl beeswax, synthetic, siliconyl and hydrogenated Beeswax, synthetic, hydrogenated and siliconyl Candelilla Wax, Synthetic, hydrogenated and siliconyl Carnauba, wax, synthetic, hydrogenated and siliconyl lemon peel wax, synthetic, siliconyl and hydrogenated soybean wax, synthetic, siliconyl and hydrogenated sunflower wax and mixtures thereof. Preferred natural and synthetic waxes are Beeswax, Microcrystalline wax, Candellila wax, Ozokerite, and mixtures thereof.

Non-limiting examples of suitable silicone waxes include, Stearyoxy trimethylsilane such as DC580 wax, C30-45 alkyl methicone available as DC AMS-C30 Cosmetic Wax, stearyoxymethyl silane available as DC Silkywax 10, C24-54 alkyl methicone such as DC ST-Wax 30, C30-45 Alkyldimethylsilyl, Polypropyl-silsesquioxane, available as DC SW-8005 resin wax, and mixtures thereof.

Particularly preferred lipophilic structurants may be selected from cetyl alcohol, stearyl alcohol, microcrystalline wax, stearyloxy trimethylsilane and mixtures thereof.

The lipophilic structurant and or lubricating member preferably comprises less than 5%, preferably less than 1% by weight and more preferably is substantially free of soap (i.e. salts of fatty acids such as C4-30 carboxylic acids) or lathering surfactants. A lathering surfactant is defined as a surfactant which when combined with water and mechanically agitated generate a foam or lather. Lathering surfactants include anionic and amphoteric lathering surfactants and mixtures thereof. Anionic lathering surfactants include sarcosinates, sulfates, sulfonate, isethionate, taurates, phosphates, lactylates, glutamates, alkali metal salts of fatty acids (i.e. soaps) having from 8 to 24 carbons, and mixtures thereof.

The lipophilic structurant is preferably slightly water insoluble, more preferably very slightly soluble, even more preferably practically insoluble according to the United States' Pharmacopeia (USP) definition in 31/NF 26 Vol. 2 General Notices, Page Xvii. According to that definition, slightly soluble means that 100 to 1000 parts of water are needed to dissolve 1 part solute and very slightly soluble means than from 1000 to 10000 parts of water are needed to dissolve 1 part of solute and practically insoluble means that greater than or equal to 10000 parts of water are needed to dissolve 1 part of solute.

Silicone Polyether Block Copolymer

According to the invention, the lubricating material further comprise from about 0.1% to about 70%, preferably from 0.1% to 60%, more preferably from about 1% to about 20%, even more preferably from about 1% to 15%, most preferably from about 1% to about 5% or alternatively from about 40% to about 60%, more preferably from about 45% to about 55%, by weight of a silicone polyether copolymer or mixtures thereof.

Silicone polyether copolymers are block copolymers of silicone, polyethylene oxide and polypropylene oxide. They may have a pendant graft structure. The silicone polyether copolymer may comprise from about 1% to 50%, by weight of polyethylene oxide, from about 20% to about 90% by weight of polypropylene oxide and from about 1% to about 20% by weight of silicone. Preferably the silicone polyether copolymer comprises at least about 40%, more preferably at least about 50%, most preferably at least about 60% by weight of polypropylene oxide. In addition, the silicone polyether copolymer preferably comprises at least about 10%, more preferably from at least about 15%, most preferably from about 15% to 30% by weight of polyethylene oxide. Furthermore, the silicone polyether block copolymer comprises from 1% to 20%, preferably 10% to 20%, more preferably about 15% by weight of silicone.

Whilst silicone polyether block copolymers are known in the art to provide a number of benefits such as foaming, defoaming, wetting, deaeration and lubricity, it has been now surprisingly found that the selection of silicone block copolymers having from 20% to 90% by weight of polypropylene and from 1% to 50% of polyethylene oxide unexpectedly provide improved lubrication whilst ensuring the required level of water dispersion and or solubility verses silicone polyether block copolymers having less or no polypropylene oxide and more polyethylene oxide. Such dispersion and solubility properties are surprisingly further improved by the inclusion of from 1% to 30% by weight of the silicone polyether block copolymer of silicone. Moreover, the use of such silicone block copolymers provides improved adhesion to the skin of the actives verses alternative materials such as copolymers of polyethylene oxide and polypropylene oxide.

The silicone polyether block copolymer may comprise from 1% to 50%, preferably from 10% to 30%, more preferably about 20% by weight of polyethylene oxide. The silicone polyether block copolymer comprises from 20% to 90%, preferably from 40% to 80%, more preferably from 50 to 80%, most preferably about 65% by weight of polypropylene oxide. The silicone polyether block copolymer comprises from 1% to 20%, preferably 10% to 20%, more preferably about 15% by weight of silicone.

The silicone polyether block copolymer preferably has a ratio of polyethylene oxide units to polypropylene oxide units of from 3.0 to 0.1, preferably from 2.0 to 0.1, more preferably from 0.6 to 0.25. The silicone polyether block copolymer preferably has a ratio of polyethylene oxide units to polypropylene oxide units to silicone units of from 20:65:15.

The silicone polyether copolymer may have a molecular weight of from about 10000 to about 19000, more preferably from about 10000 to 15000.

Suitable silicone polyether copolymers are available from Momentive under the SILWETS® trademark products including L7210, L7602, L7220, L7230, L7500, preferably L7210 and L7602. Preferably the silicone polyether block copolymer is liquid at 25° C., so that it can be provided in a liquid form for spray coating manufacturing methods. The melting point is determined according to ASTM D5440-93.

In a preferred embodiment, the silicone polyether copolymers suitable for use herein only contain repeating units of silicone, polyethylene oxide and polypropylene oxide. Silicone polyether copolymers comprising additional alkyl chains are preferably excluded.

Preferably the silicone polyether block copolymer is sparingly soluble, preferably soluble or more preferably freely soluble in water according to the United States' Pharmacopeia (USP) definition in 31/NF 26 Vol. 2 General Notices, Page Xvii. According to that definition, sparingly soluble means 30 to 1000 parts of water are needed to dissolve 1 part solute, soluble means that 10 to 30 parts of water are needed to dissolve 1 part solute and freely soluble means than from 1 to 10 parts of water are needed to dissolve 1 part of solute.

Liquid Phase

The lubricating member may further comprise in addition to the lipophilic structurant and silicone polyether block copolymer from about 10% to about 70%, preferably from about 10% to about 40%, by weight of a liquid phase. In one embodiment the liquid phase comprises a hydrophobic material or mixtures thereof. The liquid phase may provide a number of in use benefits such as lubrication, skin feel and cooling sensation.

In one embodiment the liquid phase has a melting point of 45° C. or less, preferably 40° C. or less, even more preferably 30° C. or less, most preferably 25° C. or less. The melting point is determined according to ASTM D5440-93. Preferably the liquid phase and the hydrophobic material is liquid at 25° C. The use of a liquid phase enables the materials to be readily added to the lipophilic structurant upon melting or to be added by spray coating techniques during manufacture of the lubricating member. In another preferred embodiment the hydrophobic material or mixtures thereof may be very slightly soluble and have a melting point of 45° C. or less as defined herein above and be miscible with one another. In another embodiment the melting point of the mixture of liquid phase and the lipophilic structurant is preferably from 45° C. to 5° C. less than the melting point of the water soluble polymer.

Suitable liquid phase components for use herein include for example natural oils, synthetic oils, silicone oils, petrolatum, triglycerides, butters or mixtures thereof. As used herein, the term "oil" includes, but is not limited to any non-aqueous substance that is very slightly soluble, preferably practically insoluble in water according to the United States' Pharmacopeia (USP) definition in 31/NF 26 Vol. 2 General Notices, Page Xvii. According to that definition, means that 1000 to 10000 parts of water are needed to dissolve 1 part solute and that more than 10,000 parts of water are needed to dissolve 1 part solute respectively and is liquid at 25° C. Petrolatum may be considered as a lipophilic structurant or a liquid phase due to its complex mixture of component materials. For the purposes of this invention petrolatum is considered as a liquid phase component.

The oil may be selected from natural oil, synthetic oil, silicone oil and mixtures thereof. Non-limiting examples of suitable natural oils include Acetylated Castor Oil, Acetylated Hydrogenated Castor Oil, *Actinidia Chinensis* (Kiwi), Seed Oil, Adansonia Digitata Oil, Aleurites Moluccana Seed Oil, *Anacardium Occidentale* (Cashew) Seed Oil, *Arachis Hypogaea* (Peanut) Oil, Arctium Lappa Seed Oil, Argania Spinosa Kernel Oil, Argemone Mexicana Oil, *Avena Sativa* (Oat) Kernel Oil, *Bertholletia Excelsa* Seed Oil, *Borago Officinalis* Seed Oil, *Brassica Campestris* (Rapeseed) Seed Oil, *Calophyllum Tacamahaca* Seed Oil, *Camellia Japonica* Seed Oil, *Camellia Kissi* Seed Oil, *Camellia Oleifera* Seed Oil, Canola Oil, Caprylic/Capric/Lauric Triglyceride, Caprylic/Capric/Linoleic Triglyceride, Caprylic/Caprice/Myristic/Stearic Triglyceride, Caprylic/Capric/Stearic Triglyceride, Caprylic/Capric Triglyceride, *Carthamus Tinctorius* (Hybrid Safflower) Seed Oil, *Carthamus Tinctorius* (Safflower) Seed Oil, *Carum Carvi* (Caraway) Seed Oil, *Carya Illinoensis* (Pecan) Seed Oil, Castor Oil Benzoate, *Chenopodium Quinoa* Seed Oil, *Cibotium Barometz* Oil, *Citrullus Vulgaris* (Watermelon) Seed Oil, *Cocos Nucifera* (Coconut) Oil, Cod Liver Oil, *Coffea Arabica* (Coffee) Seed Oil, *Coix Lacryma-Jobi* (Job's Tears) Seed Oil, *Corylus Americana* (Hazel) Seed Oil, *Corylus Avellana* (Hazel) Seed Oil, *Cucumis Sativus* (Cucumber) Oil, *Cucurbita Pepo* (Pumpkin) Seed Oil, *Daucus Carota Sativa* (Carrot) Seed Oil, *Elaeis Guineensis* (Palm) Kernel Oil, *Elaeis Guineensis* (Palm) Oil, *Gossypium* (Cotton) Seed Oil, *Helianthus Annuus* (Hybrid Sunflower) Oil, *Helianthus Annuus* (Sunflower) Seed Oil, *Hippophae Rhamnoides* Oil, Human Placental Lipids, Hydrogenated Canola Oil, Hydrogenated Castor Oil, Hydrogenated Castor Oil Laurate, Hydrogenated Castor Oil Triisostearate, Hydrogenated Coconut Oil, Hydrogenated Cottonseed Oil, Hydrogenated C12-18 Triglycerides, Hydrogenated Fish Oil, Hydrogenated Lard, Hydrogenated Menhaden Oil, Hydrogenated Mink Oil, Hydrogenated Olive Oil, Hydrogenated Orange Roughy Oil, Hydrogenated Palm Kernel Oil, Hydrogenated Palm Oil, Hydrogenated Peanut Oil, Hydrogenated Rapeseed Oil, Hydrogenated Shark Liver Oil, Hydrogenated Soybean Oil, Hydrogenated Sunflower Seed Oil, Hydrogenated Tallow, Hydrogenated Vegetable Oil, *Isatis Tinctoria* Seed Oil, *Juglans Regia* (Walnut) Seed Oil, Lauric/Palmitic/Oleic Triglyceride, *Umnanthes Alba* (Meadowfoam) Seed Oil, *Unum Usitatissimum* (Linseed) Seed Oil, *Lupinus Albus* Seed Oil, *Macadamia Integrifolia* Seed Oil, *Macadamia Ternifolia* Seed Oil, Maleated Soybean Oil, *Mangifera Indica* (Mango) Seed Oil, Marmot Oil, *Melaleuca Alternifolia* (Tea Tree) Leaf Oil, *Melia Azadirachta* Seed Oil, *Melissa Officinalis* (Balm Mint) Seed Oil, Menhaden Oil, Mink Oil, *Moringa pterygosperma* Seed Oil, Mortierella Oil, Neatsfoot Oil, *Nelumbium Speciosum* Flower Oil, *Nigella Sativa* Seed Oil, *Oenothera Biennis* (Evening Primrose) Oil, *Olea Europaea* (Olive) Fruit Oil, *Olea Europaea* (Olive) Husk Oil, Orange Roughy Oil, *Orbignya Cohune* Seed Oil, *Orbignya Oleifera* Seed Oil, *Oryza Sativa* (Rice) Bran Oil, *Oryza Sativa* (Rice) Germ Oil, Ostrich Oil, Oxidized Corn Oil, Oxidized Hazel Seed Oil, *Papaver Orientale* (Poppy) Seed Oil, *Passiflora*

Edulis Seed Oil, *Persea Gratissima* (Avocado) Oil, *Pistacia Vera* Seed Oil, Placental Lipids, *Prunus Amygdalus Amara* (Bitter Almond) Kernel Oil, *Prunus Amygdalus Dulcis* (Sweet Almond) Oil, *Prunus Armeniaca* (Apricot) Kernel Oil, *Prunus Avium* (Sweet Cherry) Seed Oil, *Prunus Cerasus* (Bitter Cherry) Seed Oil, *Prunus Persica* (Peach) Kernel Oil, *Pyrus Malus* (Apple) Oil, *Ribes Nigrum* (Black Currant) Seed Oil, *Ricinus Communis* (Castor) Seed Oil, *Rosa Canina* Fruit Oil, *Rosa Moschata* Seed Oil, Salmon Oil, *Salvia Hispanica* Seed Oil, *Santalum Album* (Sandalwood) Seed Oil, *Sesamum Indicum* (Sesame) Seed Oil, Shark Liver Oil, *Solanum Lycopersicum* (Tomato) Seed Oil, Soybean Lipid, Sphingolipids, *Taraktogenos Kurzii* Seed Oil, *Telphairia Pedata* Oil, Vegetable Oil, *Vitis Vinifera* (Grape) Seed Oil, *Zea Mays* (Corn) Germ Oil, *Zea Mays* (Corn) Oil mineral oil and mixtures thereof.

Suitable synthetic oils include hydrocarbons, esters, alkanes, alkenes and mixtures thereof. Non-limiting examples include isopropyl palmitate, isopropyl stearate, isohexadecane, isododecane, polyglyceryl triisostearate and mixtures thereof.

Non-limiting examples of suitable silicone oils include dimethicones (including partial esters of dimethicones and fatty acids derived from natural/synthetic oils), cyclomethicones, phenylated silicones, phenyl trimethicones, trimethyl pentaphenyl trisiloxane and mixtures thereof.

Non-limiting examples of commercially available silicone oils include Dow Corning 200 fluid, DOW CORNING® 244, DOW CORNING® 245, DOW CORNING® 344, and DOW CORNING® 345, (commercially available from DOW CORNING® Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.), the Viscasil series (sold by General Electric Company), SF 1075 methyl-phenyl fluid (sold by General Electric Company) and 556 Cosmetic Grade Fluid (sold by DOW CORNING® Corp.), Silshine 151 (sold by Momentive), and PH1555 and PH1560 (sold by DOW CORNING®).

Suitable triglycerides, may have the following formula:

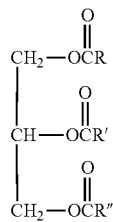

wherein R, R' and R" may be the same as or different from one or both of the others, wherein each of R, R' and R" is a fatty acid and wherein each triglyceride is solid at 25° C.

Suitable oils from which triglycerides may be formed from include, but are not limited to, the oils listed herein. Suitable fatty acids for formation of triglycerides include, but are not limited to, Myristoleic acid, Palmitoleic acid, Sapienic acid, Oleic acid, Linoleic acid, α-Linolenic acid, Arachidonic acid, Eicosapentaenoic acid, Docosahexaenoic acid, Lauric acid ($C_{12}$), Myristic acid ($C_{14}$), Palmitic acid ($C_{16}$), Stearic acid ($C_{18}$), Arachidic acid ($C_{20}$) and mixtures thereof.

Specific sources of triglycerides suitable for inclusion herein include Shea Butter, *Theobroma Cacao* (Cocoa) Seed Butter, Cocoa Butter, *Mangifera Indica* (Mango) Seed Butter, Kokum Butter and mixtures thereof. Particularly preferred are shea butter, cocoa butter and mixtures thereof.

Preferred liquid phase components may be selected from capric and or caprylic triglycerides, olive oil, shea butter, cocoa butter, petrolatum, isopropyl isostearate, dimethicones, phenylated silicones and mixtures thereof.

Water Soluble Polymer

The lubricating member further comprises from less than about 5%, preferably less than 1% and more preferably is substantially free of a water soluble polymer other than the silicone polyether block copolymer; in other words is substantially free of a water soluble silicone free polymer. Water soluble polymers such as polyethylene oxide whilst known to provide lubrication are degraded during the thermal manufacturing process and may also result in consumer relevant negative attributes.

Such water soluble polymers include polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, quaternary ammonium polymers and mixtures thereof. Such materials include the polyethylene oxides generally known as POLYOX (available from Union Carbide Corporation) or ALKOX (available from Meisei Chemical Works, Kyoto, Japan) e.g. POLYOX COAGULANT and POLYOX WSR-N-750.

Water Insoluble Polymeric Structurant

The lubricating member may also comprises less than 5% by weight preferably less than 1% by weight, more preferably is substantially free of a water insoluble polymeric structurant. Whilst not bound by theory the structuring properties of the lubricating member of the present invention are provided by the lipophlic structurant and consequently additional water insoluble polymers are not required. This enables the lubricating member to comprise higher levels of materials which deliver consumer relevant performance attributes. Such water insoluble polymeric structurants include polyethylene (PE), polypropylene, polystyrene (PS), butadiene-styrene copolymer (e.g. medium and high impact polystyrene), polyacetal, acrylonitrile-butadiene-styrene copolymer, ethylene vinyl acetate copolymer, polyurethane, and blends thereof such as polypropylene/polystyrene blend or polystyrene/impact polystyrene blend.

Optional Ingredients

In some embodiments, the lubricating material may comprise any other ingredients commonly found in commercially available shaving aid members. The lubricating member may therefore contain other conventional shaving aid ingredients, such as low molecular weight water-soluble release enhancing agents such as polyethylene glycol (MW<10,000, e.g., 1-10% by weight PEG-100), water-swellable release enhancing agents such as cross-linked polyacrylics (e.g., 2-7% by weight), colorants, skin feel/care actives, surfactants, soaps (including interrupted soaps), antioxidants, preservatives, emollients, beard softeners, astringents, medicinal agents, plasticizers, additional lubricants, depilatories/keratolytic materials, tackifiers, skin-soothing agents, fragrances, compatibilisers, anti-inflammatory agents, antipruritic/counterirritant materials, dyes, pigments etc. and mixture thereof.

Other optional components may include skin active agents such as, but not limited to oil soluble vitamins, such as vitamin E derivatives, including vitamin E acetate and tocopherol nicotinate; oil-soluble vitamin A derivatives, such as retinyl palmitate; lanolin; ceramides; sterols and sterol esters; salicylic acid; camphor; eucalyptol; essential oils; peppermint oil, Iso E Super [(1-(1,2,3,4,5,6,7,8-octahydro-2,3,8,8-tetramethyl-2-naphthalenyl)ethanonel]; and mixtures thereof. Particularly preferred are lanolin, essential oils, peppermint oil, coolants or senates and mixtures thereof. Suitable synthetic coolants include derivatives of or structurally related menthol compounds, i.e., containing the cyclohexane moiety, and derivatized with functional groups including carboxamide, ketal, ester, ether and alcohol. Nonlimiting examples include methyl emthylamido oxalate, (under the tradename FRESCOLAT® X-cool available from Symrise), menthyl lactate (such as FRESCOLAT® ML Natural available from Symrise), and Menthyl Pyrrolidone Carboxylate also known as Menthyl PCA (under the tradename QUESTICES® available from Givaudan). Optional components which are liquids are included in determining the total amount of liquid phase present.

Method of Manufacture/Processing

The lubricating member may be manufactured using a hot melt process. In such processes the lipophilic structurant is melted in a water bath to a temperature of from about 45° C. to less than 90° C., preferably about 85° C. and stirred until completely melted. The liquid silicone polyether block copolymer is then added and stirred. The temperature of the resultant mixture is then reduced to about 55° C. when the remaining components are added whilst stirring. The molten material is then transferred for example poured into a mold or container. The member can be removed from the mold or container upon cooling.

Hair Removal Head

According to some embodiments of the invention, the lubricating member finds particular application for hair removal devices. Hair removal devices generally comprise a hair removal head and a handle or grip portion, upon which the hair removal head is mounted. The hair removal device can be manual or power driven and can be used for wet and/or dry application. The hair removal head can include a wide scraping surface such as where the hair removal device is used with a depilatory, or be a razor cartridge or foil where the device is a shaving razor. The hair removal head may be replaceable and/or pivotally connected to a cartridge connecting structure and in turn or independently (e.g. permanently fixed) to a handle. In some embodiments, the cartridge connecting structure includes at least one arm to releasably engage the hair removal head.

The hair removal head typically comprises one or more elongated edges usually positioned between a first and second end, said one or more elongated edges comprising a tip extending towards said first end. Where the hair removal head is a razor cartridge the one or more elongated edges can include blades. For example, U.S. Pat. No. 7,168,173 generally describes a FUSION® razor that is commercially available from The GILLETTE® Company and which includes a razor cartridge with multiple blades. Additionally, the razor cartridge may include a guard as well as a skin engaging member. A variety of razor cartridges can be used in accordance with the present invention. Nonlimiting examples of suitable razor cartridges, with and without fins, guards, and/or shave aids, include those marketed by The GILLETTE® Company under the FUSION®, VENUS® product lines as well as those disclosed in U.S. Pat. Nos. 7,197,825, 6,449,849, 6,442,839, 6,301,785, 6,298,558; 6,161,288, and U.S. 2008/060201. Those of skill in the art will understand that the lubricating member can be used with any currently marketed system or disposable razor, including those having 2, 3, 4 or 5 blades. In such a case, the hair removal device is a razor, the hair removal head is a razor cartridge and the one or more elongated edges are blades. Another example of a hair removal device is a scraping tool for use with a hair removal composition, i.e. a depilatory.

In some embodiments, said at least one lubricating member is located on the portion of the cartridge that contacts skin during the hair removal process, forward and/or aft of the blades. A feature "forward" of the one or more elongated edges, for example, is positioned so that the surface to be treated with by the hair removal device encounters the feature before it encounters the elongated edges. A feature "aft" of the elongated edge is positioned so that the surface to be treated by the hair removal device encounters the feature after it encounters the elongated edges. Where more than one lubricating member is provided on the hair removal device, they can be the same (identical) or different, in terms of physical shape/structure and/or chemical composition.

In some particular embodiments, a plurality (e.g. 2, a first and second) of lubricating members may be provided on the hair removal head, with the first skin engaging member comprising the same composition or different. These lubricating members may be placed collectively (for example adjacent to one another) ahead of or behind the elongated edges (e.g. blades on a razor cartridge), including side by side, or separately with one ahead of the elongated edges and the other behind.

The lubricating member may be free standing utilizing a suitable attachment means such as adhesive or may be contained at least partially within a container.

The container typically has a base and at least one side wall extending vertically preferably perpendicular from said base and a skin contacting surface. In a preferred embodiment said container comprises a base and at least 2 side walls, more preferably at least 4 side walls, preferably said walls completely enclosing the base. Typically, each pair of walls are substantially parallel and preferably one pair of walls is substantially parallel to the at least two blades. Alternatively, the base may be enclosed by a one piece single wall. The container may form any shape including substantially rectangular, or oval. The container typically has a front wall adjacent the blades and a rear wall, preferably substantially parallel thereto and furthest from said blades.

The container is preferably further provided with at least one dispensing orifice for dispensing the lubricating member onto the skin during use. In one embodiment the container is provided with a top extending substantially perpendicular from the side wall (s). The container would in such an embodiment typically have a receiving region for receiving the lubricating member. The top may be substantially parallel to the base or it may be provide at an angle such that the distance of the top from the blade plane increases or decreases as the distance of the container from the blades increases. In one embodiment the height of the top of the container increases in distance from the blade plane as the container distance from the blades increases. In an alternative embodiment the height of the top of the container decreases in distance from the blade plane as the container distance from the blade increases.

The orifice may be of any shape and may, for example, have a cross sectional area of from about 0.00324 to about 1.613 $cm^2$. Small orifices can also be provided with cross sectional area of from about 0.0324 to about 0.324 $cm^2$, or from about 0.0645 to about 0.16135 $cm^2$. Larger orifices can have cross sectional areas of from about 0.324 to about 1.613 $cm^2$, or from about 0.645 to about 1.29 $cm^2$. The container may comprise a single orifice or multiple orifices which may be large and or small. In one embodiment the container comprises at least two orifices. Combinations of small and large orifices can also be provided on the same skin engaging member, or on separate members on the same cartridge, depending on the desired dispense rate and amount of exposure of the lubricating material to water. In one embodiment the top of the container is provide with one preferably two orifices, more preferably two substantially identical orifices adjacent one another.

In some embodiments, at least a portion of said container is not linear for example angled or curvilinear. Curvilinear as defined herein means that at least a portion is curved such that it does not form a straight line. Where at least two containers are provided, they can also be positioned relative to one another such that they do not form a straight line. Alternatively, the curved or angled nature is such that it forms at least a partial ring. A partial ring, as defined herein, means that the structure has at least two curved or angled sections which are concave to form an inner region. The partial ring can also include a curved or angled portion which is positioned convex to said inner region. One or more of said containers may also be positioned relative to one another to form a full ring.

The container can be formed of a variety of materials. The container may, preferably be for example, provided from a non-water soluble material such that it does not degrade or dissolve during normal use. The container typically has sufficient mechanical strength and rigidity to provide adequate mechanical strength to the entire skin engaging member, both as initially produced and after a significant amount of lubricating material has leached out of the container. Alternatively or in addition a further reinforcing member may also be utilized. In some embodiments, the container comprises a base and one or more side walls, forming a receiving region, or channel, onto or into which the lubricating material is placed.

The container may be made of a water-insoluble polymer, particularly a thermoplastic resin. Thermoplastic resins are those materials which can be extruded or molded into a shape and are resilient under normal environmental conditions such as contact with water, even up to normal household hot water temperatures (for example up to 125° C.); normal wear and tear by consumers during use; device assembly and shipping, etc. Thermoplastic resins suitable for use in the carrier include polystyrene, high impact polystyrene (polystyrene-butadiene), polypropylene, filled polypropylene, polyethylene, nylon ethylene vinyl acetate, and blends such as 70% nylon/30% polyethylene oxide, 60% polystyrene/40% polyethylene oxide butadiene styrene copolymer, polyacetal, acrylonitrile-butadiene styrene copolymer, and mixtures thereof. The preferred resins are high impact polystyrene, polystyrene, ethylene vinyl acetate (EVA), and mixtures thereof.

In some embodiments, the cartridge comprises a guard comprising at least one elongated flexible protrusion to engage a user's skin. The at least one flexible protrusion may comprise flexible fins generally parallel to said one or more elongated edges. Said at least one flexible protrusion may additionally or alternatively comprise flexible fins comprising at least one portion which is not generally parallel to said one or more elongated edges. Non-limiting examples of suitable guards include those used in current razor blades and include those disclosed in U.S. Pat. Nos. 7,607,230 and 7,024,776; (disclosing elastomeric/flexible fin bars); 2008/0034590 (disclosing curved guard fins); 2009/0049695A1 (disclosing an elastomeric guard having guard forming at least one passage extending between an upper surface and a lower surface). In some embodiments, said lubricating member is positioned on the cartridge aft of the guard and forward of said elongated edge. In another embodiment, the lubricating member is positioned on the cartridge forward of the guard. This embodiment can be particularly useful to deliver the lubricating member prior to contact with the guard.

EXAMPLE FORMULATIONS

The following comparative example 1(A) and E and inventive examples (B, C, D and F) were prepared and sensory tested conducted as outlined below:
Sensory Protocol Sensory testing was conducted upon a naive panel (N=5) with 3 non-overlapping strokes being performed on their forearms for both examples. The order in which each panelist received the products and the first forearms used were randomized The procedure used was as follows;
1. Wash both forearms thoroughly with warm water and soap to remove any oils or moisturizers that may already be on the skin.
2. Place product in water for 100 seconds (preheated to 40° C.)
3. Rinse one arm using water in the beaker provided (50 ml-preheated to 40° C.)
4. Take 3 non overlapping strokes on the rinsed area using the first product supplied.
5. Immediately assess lubrication of the product on a scale of 0-10; 0 being extremely draggy/not lubricated and 10 being extremely lubricating/slippery.
6. By using your finger assess the skin condition on a scale of 0-10, 0 being sticky and 10 being not sticky.
7. Rinse fore-arm with 50 ml of water in a beaker (pre heated to 40° C.) and pat dry three times with a paper towel and wait for 2 mins. Then assess skin for sticky and not sticky on a 0-10 scale; 0 being sticky/greasy and 10 being not sticky and for rough and smooth on a 0-10 scale of 0 being rough and 10 smooth.
8. Identify preferred product.
9. After 10 mins reassess the skin, which product results in softer skin.

The above protocol was used for all sensory tests below.

Comparative Example A & Inventive Example B

| Ingredient | Comparative A (%) | Inventive B (%) |
|---|---|---|
| Dimethicone, 350 cst * | 20 | — |
| Silwet L7210 ** | — | 20 |
| Cetyl alcohol | 60 | 60 |
| Silicone wax, DC580 ** | 20 | 20 |

Sourced from:
* Dow Corning
** Momentive

Comparative Example A and Inventive Example B were prepared as follows:
1. Sanitize all equipment
2. Turn on water bath/vessel jacket to 85° C.
3. Add lipophilic structurants (cetyl alcohol, multiwax 180MH, DC580 silicone wax) and stir with overhead stirrer until completely melted
4. Add liquid phase ingredients (petrolatum, DC200, mineral oil, isopropyl isostearate) and mix until fully liquid
5. Cool and pour mixture into a mould or container 6. For sensory testing, mould chemistry onto razor analogue and attach to razor handle. Chemistry to be of a suitable size for use in shaving (33mm long×3mm wide)

Product A=Comparative Example A;

Product B=Inventive Example B;

Test panel participants N=1-5 were tested in accordance with the sensory protocol described above.

| Attribute | Test products | | | | | | | | | |
|---|---|---|---|---|---|---|---|---|---|---|
| | 1A | 1B | 2A | 2B | 3A | 3B | 4A | 4B | 5A | 5B |
| Non overlap lubrication | 2 | 3 | 3 | 3 | 1 | 1 | 5 | 5 | 4 | 6 |
| Over stroke lubrication | 2 | 4 | 4 | 6 | 3 | 5 | 5 | 7 | 7 | 8 |
| Before rinse sticky | 8 | 8 | 9 | 9 | 7 | 8 | 10 | 10 | 10 | 10 |
| After dry sticky | 10 | 10 | 10 | 10 | 10 | 10 | 10 | 10 | 10 | 10 |
| After dry soft | 7 | 8 | 6 | 6 | 9 | 10 | 5 | 7 | 4 | 6 |
| Preference | | IB | | B | | B | | B | | B |

As can be seen from the data all the test participants preferred the inventive example versus the comparative sample, demonstrating the advantage for the inclusion of SILWET®; All of the panelists preferred the inventive example for glide; 2 out of 5 had a preference for the inventive example for lubrication on first non-overlapping strokes and; all panelists preferred the inventive example for lubrication on over-strokes. Neither formulation was found to be sticky after rinsing. The inventive sample was preferred for being soft after drying.

Inventive Example C & D

| Ingredient | C (%) | D (%) |
|---|---|---|
| Silwet L7210 | 57 | — |
| Silwet L7602 | — | 57 |
| Multiwax MH 180 $ | 7 | 7 |
| Cetyl alcohol | 36 | 36 |

Sourced from:
$ Sonnenborn

Inventive examples C and D were prepared as for Inventive Example B described above and tested according to the sensory protocol described above.

| Attribute | Test products | | | | | | | | | |
|---|---|---|---|---|---|---|---|---|---|---|
| | 1C | 1D | 2C | 2D | 3C | 3D | 4C | 4D | 5C | 5D |
| Non overlap lubrication | 4 | 5 | 3 | 2 | 2 | 1 | 4 | 5 | 3 | 2 |
| Over stroke lubrication | 5 | 6 | 5 | 4 | 3 | 2 | 5 | 6 | 4 | 4 |
| Before rinse sticky | 9 | 8 | 9 | 8 | 8 | 9 | 10 | 10 | 10 | 10 |
| After dry sticky | 10 | 10 | 10 | 10 | 10 | 10 | 8 | 9 | 10 | 10 |
| After dry soft | 5 | 5 | 7 | 7 | 8 | 7 | 5 | 7 | 8 | 6 |
| Preference | | D | C | | C | | | D | | D |

As can be seen from the data there was no preference for one inventive example versus the other inventive example across the test participants. This demonstrates that the two polyether copolymer materials (silwets) used provide similar performance Comparative Example E

| Ingredient | E % |
|---|---|
| Petrolatum | 40.25 |
| Mineral Oil | 40.25 |
| Kraton G1650E £ | 5 |
| Thixin R ^ | 2 |
| Parraffin Wax SP206 & | 7.5 |
| Steareth-2 | 5 |

Sourced from:
£ Kraton,
& Strahl and Pitsch,
^ Elementis

Comparative example E which is presentative of the prior art comprising a modifying surfactant and a hydrophobic phase was prepared in accordance with the making instructions disclosed in WO2012/148939; Example 1.

Inventive Example F

| Ingredient | F % |
|---|---|
| Silwet L7210 | 57 |
| Cetyl alcohol | 36 |
| Multiwax MH 180 | 7 |

Inventive example F was prepared in accordance with the making instructions as for Inventive Example B. Comparative example E and inventive example F were tested according to the sensory testing protocol described above.

| Attribute | 1E | 1F | 2E | 2F | 3E | 3F | 4E | 4F | 5E | 5F |
|---|---|---|---|---|---|---|---|---|---|---|
| Non overlap lubrication | 2 | 3 | 3 | 3 | 1 | 2.5 | 3 | 7 | 2 | 4 |
| Over stroke lubrication | 2 | 3 | 4 | 6 | 3 | 4 | 3 | 7 | 3 | 5 |
| Before rinse sticky | 8 | 10 | 10 | 10 | 5 | 10 | 9 | 10 | 10 | 10 |
| After dry sticky | 10 | 10 | 10 | 10 | 10 | 10 | 10 | 10 | 10 | 10 |
| After dry soft | 6 | 6 | 6 | 6 | 6 | 8 | 8 | 7 | 7 | 4 |
| Preference | | F | | F | | F | | F | | F |

As can be seen from the data all the test participants preferred the inventive example versus the prior art example; all of the panellists preferred the inventive example for glide, 4 out of 5 had a preference for the inventive example for lubrication on first non-overlapping strokes; all panellists preferred the inventive example for lubrication on over-strokes. Neither formulation was found to be sticky after rinsing.

Inventive Examples G-K

| Ingredient | G (%) | H (%) | J (%) | K (%) |
|---|---|---|---|---|
| Cetyl Alcohol | 50 | 50 | 50 | 50 |
| Multiwax MH180 | 10 | 10 | 10 | 10 |
| Petrolatum | 10 | 10 | — | 20 |
| Silwet L7210 | 20 | 20 | 20 | 20 |
| Mineral Oil | 10 | — | 20 | — |
| Schercemol 318 (isopropyl isostearate) # | — | 10 | — | — |

- Lubrizol

Inventive examples G-K were prepared in accordance with the making instructions as for Inventive Example B.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition of the same term in a document incorporated by reference, the meaning of definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A razor cartridge comprising:
   a) a razor cartridge housing containing at least one blade;
   b) a guard member positioned on the razor cartridge housing forward of the at least one blade;
   c) a cap positioned on the razor cartridge housing aft of the at least one blade, wherein during a shaving stroke skin is contacted by the guard prior to the at least one blade, and the at least one blade prior to contacting the cap; said cap comprising at least one lubricating member, each lubricating member comprising:
      i) from about 25% to about 65% by weight of said lubricating member of a lipophilic structurant or mixture thereof, wherein said lipophilic structurant is selected from C14-C20 alcohols, microcrystalline wax, stearyloxytrimethylsilane, and mixtures thereof,
      ii) from about 20% to about 60% by weight of said lubricating member of a silicone polyether block copolymer, wherein said silicone polyether block copolymer consists essentially of repeating units of polyethylene oxide, silicone, and polypropylene oxide, at levels of: about 1% to about 50%, by weight of polyethylene oxide, from about 20% to about 90% by weight of polypropylene oxide and from about 1% to about 20% by weight of silicone, and has a ratio of polyethylene oxide units to polypropylene oxide units to silicone units of from 20:65:15, and
      iii) from about 20% to about 40% by weight of said lubricating member of a liquid phase, wherein said liquid phase comprises a component selected from natural oil, synthetic oil, natural butter, triglyceride, petrolatum, silicone, and mixtures thereof;
      iv) wherein said silicone polyether block copolymer is free of any additional alkyl chains; and
      v) wherein said lubricating member is substantially free of soap.

2. The razor cartridge according to claim 1, wherein said lipophilic structurant has a melting point of at least about 45° C.

3. The razor cartridge according to claim 1, wherein said lipophilic structurant has a melting point of from at least about 45° C. to less than about 90° C.

4. The razor cartridge according to claim 1, wherein said silicone polyether block copolymer has a molecular weight of from about 600 to about 30000.

5. The razor cartridge according to claim 1, wherein said silicone polyether block copolymer has a molecular weight of from about 10000 to about 19000.

6. The razor cartridge according to claim 1, wherein said lipophilic structurant is selected from cetyl alcohol, stearyl alcohol, and mixtures thereof.

7. The razor cartridge according to claim 1, wherein said lubricating member comprises a hydrophobic liquid phase.

8. The razor cartridge according to claim 1, wherein said liquid phase comprises a material selected from capric and or caprylic triglycerides, olive oil, shea butter, cocoa butter, isopropyl isostearate, petrolatum, dimethicone, phenylated silicones and mixtures thereof.

9. The razor cartridge according to claim 1, wherein said liquid phase has a melting point of less than about 40° C.

10. The razor cartridge according to claim 1, wherein said liquid phase has a melting point of less than about 30° C.

11. The razor cartridge according to claim 1, wherein said lubricating member comprises less than about 5% by weight of a water insoluble polymeric structurant.

12. The razor cartridge according to claim 1, wherein said lubricating member comprises less than about 1% by weight of a water insoluble polymeric structurant.

13. A method of manufacturing a lubricating member for use on a razor cartridge according to claim 1, comprising the steps of;
   a) Melting said lipophilic structurant to a temperature of about 85° C. and stirring;
   b) Adding said silicone polyether block copolymer and stirring;
   c) Cooling the temperature of the resultant mixture to about 55° C.;
   d) Adding said liquid phase and any remaining optional components to said resultant mixture whilst stirring; and
   e) Transferring the molten mixture into a mold or container.

14. A razor cartridge comprising:
   a) a razor cartridge housing containing at least one blade;
   b) a guard member positioned on the razor cartridge housing forward of the at least one blade;
   c) a cap positioned on the razor cartridge housing aft of the at least one blade, wherein during a shaving stroke skin is contacted by the guard prior to the at least one blade, and the at least one blade prior to contacting the cap; said cap comprising at least one lubricating member, each lubricating member comprising:
      i) from about 10% to about 80% by weight of said lubricating member of a lipophilic structurant or mixture thereof,
      ii) from about 0.1% to about 60% by weight of a silicone polyether block copolymer of said lubricating member, wherein said silicone polyether block copolymer consists essentially of repeating units of polyethylene oxide, silicone, and polypropylene oxide, at levels of: about 1% to about 50%, by weight of polyethylene oxide, from about 20% to about 90% by weight of polypropylene oxide and from about 1% to about 20% by weight of silicone, and has a ratio of polyethylene oxide units to polypropylene oxide units to silicone units of from 20:65:15, and
iii) from about 10% to about 70% by weight of a liquid phase of said lubricating member;
iv) wherein said silicone polyether block copolymer is free of any additional alkyl chains;
v) wherein said lubricating member is substantially free of soap, and
vi) wherein each lubricating member is formed by mixing said lipophilic structurant, said silicone polyether block copolymer, and said liquid phase.

* * * * *